United States Patent
Puntambekar

(10) Patent No.: US 8,628,968 B2
(45) Date of Patent: Jan. 14, 2014

(54) ETHYLENE OXIDE STERILIZATION INDICATOR COMPOSITIONS

(75) Inventor: Shobha Shakher Puntambekar, Morganville, NJ (US)

(73) Assignee: La-Co Industries, Inc., Elk Grove Village, IL (US)

( * ) Notice: Subject to any disclaimer, the term of this patent is extended or adjusted under 35 U.S.C. 154(b) by 7 days.

(21) Appl. No.: 13/432,817

(22) Filed: Mar. 28, 2012

(65) Prior Publication Data

US 2012/0252125 A1 Oct. 4, 2012

Related U.S. Application Data

(60) Provisional application No. 61/469,410, filed on Mar. 30, 2011.

(51) Int. Cl.
G01N 31/22 (2006.01)

(52) U.S. Cl.
USPC .............................................. 436/1

(58) Field of Classification Search
USPC .............................................. 436/1
See application file for complete search history.

(56) References Cited

U.S. PATENT DOCUMENTS

| | | | | |
|---|---|---|---|---|
| 2,830,994 A | * | 4/1958 | Gasson | 546/324 |
| 3,627,469 A | * | 12/1971 | Cheng | 436/1 |
| 3,678,055 A | * | 7/1972 | Passal et al. | 546/286 |
| 3,919,056 A | * | 11/1975 | Habulak | 205/310 |
| 3,950,547 A | * | 4/1976 | Lamar et al. | 426/74 |
| 3,957,804 A | * | 5/1976 | Ishioka et al. | 546/317 |
| 3,992,154 A | * | 11/1976 | Whitbourne et al. | 422/34 |
| 4,082,846 A | * | 4/1978 | Clark | 514/354 |
| 4,094,642 A | | 6/1978 | Sumimoto et al. | |
| 4,096,240 A | * | 6/1978 | Mathur | 424/59 |
| 4,383,073 A | * | 5/1983 | Wessling et al. | 525/486 |
| 4,407,960 A | * | 10/1983 | Tratnyek | 436/1 |
| 4,436,819 A | * | 3/1984 | Manning | 436/1 |
| 4,671,936 A | * | 6/1987 | Barron | 422/416 |
| 4,678,640 A | * | 7/1987 | Hamano et al. | 422/401 |
| 4,826,772 A | * | 5/1989 | Meathrel | 436/93 |
| 5,258,065 A | * | 11/1993 | Fujisawa | 524/35 |
| 5,340,537 A | | 8/1994 | Barrett | |
| 6,488,890 B1 | * | 12/2002 | Kirckof | 422/403 |
| 6,800,124 B2 | | 10/2004 | Puntambekar | |
| 7,141,214 B2 | | 11/2006 | Puntambekar | |
| 2002/0121629 A1 | * | 9/2002 | Mikumo et al. | 252/408.1 |
| 2005/0142094 A1 | | 6/2005 | Kumar | |
| 2009/0123332 A1 | * | 5/2009 | Whitehead et al. | 422/27 |

FOREIGN PATENT DOCUMENTS

| | | |
|---|---|---|
| WO | 0110476 | 2/2001 |
| WO | 2009113197 | 9/2009 |
| WO | 2009149243 | 12/2009 |

OTHER PUBLICATIONS

NETQEM product information for 1[4-Nitrobenzoyl]-4-Carboxypyridylhydrazide, Copyright 2009, downloaded from http://www.netqem.us/product.php?id=1131&cid=7[May, 28, 2013 8:02:09 PM].*

* cited by examiner

*Primary Examiner* — Arlen Soderquist
(74) *Attorney, Agent, or Firm* — McDermott Will & Emery LLP

(57) ABSTRACT

An indicator composition for indicating that an article has undergone an ethylene oxide sterilization process is provided. The indicator composition includes at least one pyridine derivative that reacts with moist ethylene oxide to provide an irreversible color change of the composition.

4 Claims, No Drawings

ETHYLENE OXIDE STERILIZATION INDICATOR COMPOSITIONS

CROSS-REFERENCE TO RELATED APPLICATION DATA

This application claims the benefit of priority of Provisional U.S. Patent Application Ser. No. 61/469,410, filed Mar. 30, 2011, the disclosure of which is incorporated herein by reference in its entirety.

BACKGROUND OF THE INVENTION

The present invention pertains to sterilization indicators, more particularly, to indicator compositions that change color when exposed to ethylene oxide sterilization conditions.

Instruments and materials used in modern medical facilities such as hospitals, medical laboratories and other health service facilities, often require sterilization. Sterilization can be achieved by variety of technologies, such as steam sterilization, ethylene oxide gas sterilization, formaldehyde gas sterilization, plasma sterilization and ozone sterilization processes. Although steam sterilization is effective, it is not always appropriate, for example, for heat-sensitive materials such as biological materials, fiber optics, electronics, and many plastics.

Ethylene oxide sterilization is a common alternative to steam sterilization for such heat-sensitive objects and materials. Ethylene oxide gas used in ethylene oxide sterilization processes is a widely used alkylating agent, which can be used alone or in an admixture with an inert gaseous diluent such as carbon dioxide, nitrogen, trichloromonofluoromethane, dichlorodifluoromethane, and the like. Ethylene oxide gas can be used as a sporicidal and virucidal agent. Consequently, ethylene oxide sterilization is often employed to ensure total eradication of microorganisms.

Since ethylene oxide gas can readily diffuse through commonly employed packaging materials and is highly effective in killing microorganisms at temperature well below those required for heat or steam sterilization techniques, it enables efficient sterilization of many items, particularly those made of thermoplastic materials, which can be damaged under heat or steam sterilization conditions. Ethylene oxide sterilization generally involves placing an item in a chamber and subjecting it to ethylene oxide vapor. When used properly, ethylene oxide is not only lethal to all known microorganisms at ordinary temperature, but it is also non-corrosive, readily removed by aeration, easily handed and stored, and has a low toxicity to humans.

Various indicators for indicating that an article has undergone ethylene oxide sterilization are commercially available. For example, water-based ethylene oxide sterilization indicator inks and methods are disclosed in U.S. Pat. No. 6,800,124 and U.S. Pat. No. 7,141,214, which are assigned to the assignee of the present application, and incorporated herein by reference in their entirety.

The present invention provides improved methods and indicator compositions for indicating successful sterilization of articles by ethylene oxide sterilization.

BRIEF SUMMARY OF THE INVENTION

In one aspect, an indicator composition for ethylene oxide sterilization processes including at least one pyridine derivative is provided. In one embodiment, the pyridine derivative is selected from a group consisting of 1-p-nitrobenzoyl-1,4-carboxypyridylhydrazide, niacinamide, isoniazid, 1-3-di-4-pyridyl propane, and combinations thereof. The indicator composition can further include a solvent, coloring material(s), binder(s) and other additives.

In another aspect, the indicator composition undergoes an irreversible color change when exposed to ethylene oxide vapor in the presence of low-temperature steam after 30 minutes at 30° C. or 20 minutes at 54° C. The indicator composition according to some embodiments of the present invention does not change color when exposed to steam for 10 min at 121° C., or 2 min at 134° C., or exposed to dry heat for 30 min at 140° C.

In a different embodiment, the indicator composition includes between about 10% and about 15% by weight of 1-p-nitrobenzoyl-1,4-carboxypyridylhydrazide and between about 10% and about 15% by weight of niacinamide.

These and other features and advantages of the present invention will be apparent from the following detailed description, in conjunction with the appended claims.

DETAILED DESCRIPTION OF THE INVENTION

While the present invention is susceptible of embodiment in various forms, presently preferred embodiments are described herein with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

According to an embodiment of the present invention, a chemical indicator composition for indicating successful sterilization of articles by an ethylene oxide sterilization process is provided. The indicator composition includes at least one pyridine derivative as an active chemical reactant. In such an indicator composition, the pyridine derivative undergoes an alkylation reaction with ethylene oxide (EtO) under EtO sterilization conditions. The indicator composition can be prepared by dispersing the pyridine derivative in a suitable solvent along with other components, such as a coloring material, a binder, a thickener, and a surfactant. After being exposed to ethylene oxide sterilization process, indicator gives a color change to dark brown or black.

Suitable pyridine derivative include, but not limited to, 1-p-nitrobenzoyl-1,4-carboxypyridylhydrazide, niacinamide, isoniazid, and 1-3-di-4-pyridyl propane. The indicator compound can include a pyridine derivative or a combination of pyridine derivatives. For example, an indicator compound can include 1-p-nitrobenzoyl-1,4-carboxypyridylhydrazide and niacinamide.

The indicator composition can further include one or more coloring materials. For example, a red color material can be added to make an indicator that has an initial color of red, which turns to dark brown or black after a successful EtO sterilization process. Suitable coloring materials include, but not limited to, 615 Red—Savinyl Fire Red 3GLS, phthalocyaine blue 110E, Vossen blue, cinquasia red B NRT 742-D, Tint-AYD-CW-5673-deep organic red, sunglow yellow g1230, and sunglow yellow 1210.

Further, the indicator composition can include binders, thickeners, surfactants, and various other additives used in traditional indicator compositions to form an indicator ink that can be applied on various substrates.

The indicator compositions of various embodiments of the present invention are formulated to pass the requirements for EtO sterilization tested according to ISO 11140-1:2005(E).

When tested according to ISO 11140-1:2005(E), the indicator compositions do not change color when exposed to EtO gas in 60% relative humidity (RH) for 5 minutes at 30° C. or for 2 minutes at 54° C. However, the color of indicators, which may be red, blue, white, etc. initially, changes irreversibly to dark brown or black after being exposed to EtO in 60% RH for 30 min at 30° C. or for 20 minutes at 54° C., indicating successful sterilization of articles.

An indicator can be a dual indicator including a steam sterilization indicator composition and an EtO sterilization indicator composition. In one embodiment, the dual indicator includes a strip of the steam sterilization indicator composition and a strip of the EtO sterilization indicator composition, which are printed on the same substrate. Such dual indicators can be convenient for users utilizing both steam and EtO sterilization processes, as the users need not purchase two different indicators. Further, the dual indicators can eliminate a risk of user using a wrong indicator. However, some commercially available dual indicators had drawbacks in that the EtO sterilization indicator composition was observed to transfer to articles when exposed to steam sterilization conditions.

Thus, in one embodiment, the EtO sterilization indicator composition is formulated to minimize any such transfer under the steam sterilization conditions. The indicator compositions includes 1-p-nitrobenzoyl-1,4-carboxypyridylhydrazide and niacinamide as active chemical reactants that undergo alkylation reaction with moist EtO during the EtO sterilization process. Ingredients and an amount of each ingredient and a function of each ingredient in the indicator composition are shown in Table 1.

TABLE 1

Ingredients of an Indicator Composition

| Ingredient | Amount (wt. %) | Function |
| --- | --- | --- |
| 1-p Nitrobenzoyl-1,4-carboxypyridylhydrazide (cas # 79771-29-2) | 10-15 | Active chemical reacts with ETO |
| Nicotinic acid amide (cas # 98-92-0) | 10-15 | Active chemical reacts with ETO |
| 615 red Cobalt based pigment (proprietory) | 0-0.2 | Coloring material |
| Shellac (cas # 9000-59-3) | 5-10 | Binder |
| Ethocel-Std(cas # 9004-57-3) | 1-5 | Binder + thickener |
| Fumed silica (cas # 112945-52-5) | 1-2 | Additive thickener |
| Triton-X-100 cas# 9002-93-1) | 0.5-1 | surfactant |
| N-propyl acetate (cas#109-60-4) | 20-25 | solvent |
| N-propyl Alcohol (cas # 71-23-8) | 20-25 | solvent |
| Glycol Ether (cas # 107-98-2) | 15-20 | solvent |

This indicator composition does not change color when exposed to EtO gas in 60% relative humidity (RH) for 5 minutes at 30° C. or for 2 minutes at 54° C. However, the color of the indicator composition, which is red initially, changes irreversibly to dark brown or black after being exposed to EtO in 60% RH for 30 min at 30° C. or for 20 minutes at 54° C., indicating successful sterilization of articles. Thus, the indicator composition passes the EtO sterilization requirements of Table 1 tested according to ISO 11140-1:2005(E). Further, indicator composition does not change color after being exposed to steam for 10 min at 121° C., or 2 min at 134° C., or exposed to dry heat for 30 min at 140° C.

All patents referred to herein, are hereby incorporated herein by reference, whether or not specifically do so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An indicator composition for ethylene oxide sterilization processes comprising at least one pyridine derivative, wherein the at least one pyridine derivative is a combination of 1-p-nitrobenzoyl-1,4-carboxypyridylhydrazide and niacinamide, wherein the 1-p-nitrobenzoyl-1,4-carboxypyridylhydrazide comprises between about 10% and about 15% by weight of the indicator composition, and wherein the niacinamide comprises between about 10% and about 15% by weight of the indicator composition.

2. The indicator composition of claim 1, further including a solvent, a coloring material, and a binder.

3. The indicator composition of claim 1, wherein the indicator composition undergoes an irreversible color change when exposed to ethylene oxide vapor in the presence of low-temperature steam after 30 minutes at 30° C. or 20 minutes at 54° C.

4. The indicator composition of claim 1, wherein the indicator composition does not change color when exposed to steam for 10 min at 121° C. or 2 min at 134° C.; or exposed to dry heat for 30 min at 140° C.

* * * * *